United States Patent [19]

Ramm et al.

[11] 4,254,123

[45] Mar. 3, 1981

[54] NOVEL IMIDAZOQUINOXALINES

[75] Inventors: Peter J. Ramm, Newcastle-upon-Tyne; Alan C. Barnes, Cirencester Glos., both of England

[73] Assignee: Roussel Uclaf, Paris, France

[21] Appl. No.: 61,626

[22] Filed: Jul. 30, 1979

[30] Foreign Application Priority Data

Aug. 2, 1978 [GB] United Kingdom ............... 31934/78

[51] Int. Cl.³ .................... A61K 31/495; C07D 487/14
[52] U.S. Cl. .................................... 424/250; 424/245;
544/225; 544/346
[58] Field of Search ................ 544/225, 346; 424/245, 424/250

[56] References Cited

U.S. PATENT DOCUMENTS

| | | | |
|---|---|---|---|
| 3,887,566 | 6/1975 | Rodway et al. ................ | 544/346 X |
| 4,075,343 | 2/1978 | Kadin ................................ | 424/258 |
| 4,145,419 | 3/1979 | Rowlands et al. ............... | 424/248.4 |
| 4,151,280 | 4/1979 | Rowlands et al. ............... | 424/250 |
| 4,160,097 | 7/1979 | Warner, Jr. et al. ............ | 544/346 X |

*Primary Examiner*—Donald G. Daus

*Assistant Examiner*—Diana G. Rivers
*Attorney, Agent, or Firm*—Hammond & Littell, Weissenberger and Muserlian

[57] ABSTRACT

Novel imidazoquinoxalines of the formula

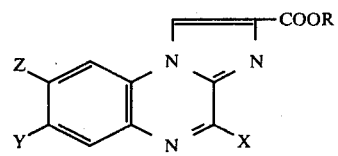

wherein R is selected from the group consisting of hydrogen, alkyl of 1 to 5 carbon atoms, —NH$_4$, alkali metal, alkaline earth metal, magnesium, aluminum and non-toxic, pharmaceutically acceptable amines, X is selected from the group consisting of hydrogen, alkoxy of 1 to 5 carbon atoms and carbamoyl and Y and Z are individually selected from the group consisting of hydrogen and halogen and their non-toxic, pharmaceutically acceptable acid addition salts having anti-allergic activity and their preparation.

39 Claims, No Drawings

NOVEL IMIDAZOQUINOXALINES

STATE OF THE ART

Related compounds are described in U.S. Pat. Nos. 4,075,343, 4,145,419 and 4,151,280 as well as in copending, commonly assigned U.S. patent application Ser. No. 869,842 filed Jan. 16, 1978 and Ser. No. 958,561 filed Nov. 7, 1978.

OBJECTS OF THE INVENTION

It is an object of the invention to provide the novel quinoxalines of formula I and their non-toxic, pharmaceutically acceptable acid addition salts and a novel process for their preparation.

It is another object of the invention to provide novel antiallergic compositions and to provide a novel method of relieving allergic symptoms in warm-blooded animals.

These and other objects and advantages of the invention will become obvious from the following detailed description.

THE INVENTION

The novel quinoxalines of the invention are selected from the group consisting of imidazoquinoxalines of the formula

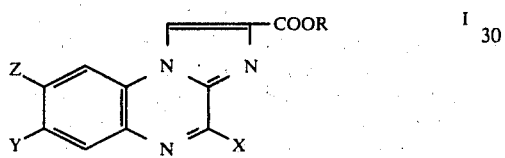

wherein R is selected from the group consisting of hydrogen, alkyl of 1 to 5 carbon atoms, —NH$_4$, alkali metal, alkaline earth metal, magnesium, aluminum and non-toxic, pharmaceutically acceptable amines, X is selected from the group consisting of hydrogen, alkoxy of 1 to 5 carbon atoms and carbamoyl and Y and Z are individually selected from the group consisting of hydrogen and halogen and their non-toxic, pharmaceutically acceptable acid addition salts.

Examples of R are hydrogen; alkyl of 1 to 5 carbon atoms such as methyl, ethyl, propyl, isopropyl, butyl, isobutyl, tert-butyl or pentyl; alkali metals such as sodium, potassium or lithium, alkaline earth metals such as calcium; magnesium; aluminum, —NH$_4$ and amines such as lysine, arginine, triethanolamine or tris-(hydroxymethyl)-aminomethane. Examples of X are hydrogen, carbamoyl or alkoxy of 1 to 5 carbon atoms such as methoxy, ethoxy, propoxy, isopropoxy, butoxy, isobutoxy, tert.-butoxy, or pentoxy. Examples of X and Y are hydrogen, chlorine or bromine.

Examples of suitable acids for the non-toxic, pharmaceutically acceptable acid addition salts are inorganic acids such as hydrochloric acid, hydrobromic acid, hydroiodic acid, nitric acid or sulfuric acid and organic acids such as acetic acid, formic acid, benzoic acid, maleic acid, fumaric acid, succinic acid, tartaric acid, citric acid, oxalic acid, glyoxalic acid or aspartic acid, alkane sulfonic acids and aryl sulfonic acids such as methane sulfonic acid or benzene sulfonic acid.

Among the preferred compounds of formula I are those wherein R is hydrogen or ethyl, those wherein X is hydrogen or ethoxy, those wherein X and Y are individually hydrogen or chlorine and their salts and their non-toxic, pharmaceutically acceptable acid addition salts. Especially preferred are those wherein R is hydrogen, X is hydrogen or ethoxy and X and Y are individually chlorine or hydrogen and those wherein R, X and Z are hydrogen and Y is hydrogen or chlorine and their salts.

Specific preferred compounds of formula I are imidazo-[1,2-a]-quinoxaline-2-carboxylic acid, ethyl 7,8-dichloro-imidazo-[1,2-a]-quinoxaline-2-carboxylate, 7,8-dichloro-imidazo-[1,2-a]-quinoxaline-2-carboxylic acid, 7-chloro-imidazo-[1,2-a]-quinoxaline-2-carboxylic acid, 8-chloro-imidazo-[1,2-a]-quinoxaline-2-carboxylic acid, 4-ethoxy-imidazo-[1,2-a]-quinoxaline-2-carboxylic acid, and 4-carbamoyl-imidazo-[1,2-a]-quinoxaline-2-carboxylic acid, and salts thereof and especially tri-(hydroxymethyl)-methylammonium imidazo-[1,2-a]-quinoxaline-2-carboxylate and sodium imidazo-[1,2-a]-quinoxaline-2-carboxylate.

The novel process of the invention for the preparation of the compounds of formula I wherein R is alkyl of 1 to 5 carbon atoms comprises subjecting a compound of the formula

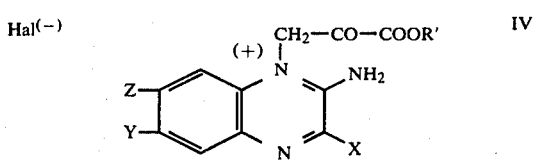

wherein X, Y and Z have the above definition and R' is alkyl of 1 to 5 carbon atoms and Hal is a halogen such as chlorine and bromine to cyclization conditions to obtain the desired compound of formula I. Cyclization is preferably effected by heating such as at reflux in an organic solvent such as an alkanol of 1 to 5 carbon atoms, i.e. ethanol.

The compounds of formula IV may be prepared by reacting a compound of the formula

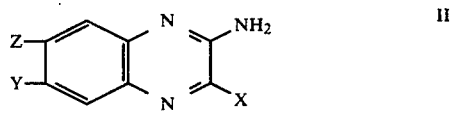

wherein X, Y and Z have the above definitions with a compound of the formula

wherein Hal and R' have the above definition. The reaction is preferably effected in an organic solvent such as dimethoxyethane or tetrahydrofuran.

The process of the invention for the preparation of compounds of formula I wherein R is hydrogen comprises subjecting a compound of formula I wherein R is alkyl of 1 to 5 carbon atoms to hydrolysis, preferably with an alkali metal hydroxide such as sodium hydroxide or potassium hydroxide. The said acid may then be salified with any appropriate base. The acid addition salts may be prepared by reacting the compound of formula I with a substantially equimolar amount of an organic or inorganic acid.

The novel anti-allergic compositions of the invention are comprised of an anti-allergically effective amount of at least one compound of formula I and its non-toxic, pharmaceutically acceptable acid addition salts and an inert pharmaceutical carrier or excipient. The compositions may be in the form of tablets, coated tablets, gelatin capsules, granules, suppositories, syrups, aerosols, creams, ointments or injectable solutions or suspensions.

Examples of suitable excipients are talc, arabic gum, lactose, starch, magnesium stearate, cocao butter, aqueous and non-aqueous vehicles, fatty substances of animal or vegetable origin, paraffinic derivatives, glycols, wetting agents, dispersants or emulsifiers and preservatives.

The compositions are useful for the treatment of asthma and bronchial asthma of allergic origin.

The novel method of the invention for relieving allergic symptoms in warm-blooded animals, including humans, comprises administering to warm-blooded animals an anti-allergically effective amount of at least one compound of formula I and its non-toxic, pharmaceutically acceptable acid addition salts. The compounds may be administered orally, rectally, parenterally or topically to the skin or mucous. The usual daily dose is 0,005 to 2 mg/kg depending on the compound and method of administration.

In the following examples there are described several preferred embodiments to illustrate the invention. However, it is to be understood that the invention is not intended to be limited to the specific embodiments.

EXAMPLE 1

Imidazo-[1,2-a]-quinoxaline-2-carboxylic acid

STEP A: 1-carbethoxy-carbonylmethyl-2-amio-quinoxalinium bromide

A solution of 0.9 g of 2-amino-quinoxaline, 1.25 g of ethyl bromopyruvate and 25 ml of dimethoxyethane was stirred overnight at room temperature and was filtered to recover 1.58 g of 1-carbethoxy-carbonylmethyl-2-amino-quinoxalinium bromide as a pale yellow crystalline solid.

STEP B: ethyl imidazo-[1,2-a]-quinoxaline-2-carboxylate

A suspension of 0.4 g of the product of Step A and 15 ml of ethanol was refluxed for 2 hours and the resulting clear orange solution was concentrated to half of its original volume. The mixture was filtered to recover 0.25 g of ethyl imidazo-[1,2-a]-quinoxaline-2-carboxylate as a pale yellow crystalline solid which melted at 184°–187° C. after crystallization from an ether-methanol mixture as soft white needles.

Analysis: $C_{13}H_{11}N_3O_2$: Calculated: %C 64.72; %H 4.60; %N 17.42. Found: %C 64.80; %H 4.66; %N 17.47.

STEP C: Imidazo-[1,2-a]-quinoxaline-2-carboxylic acid 10 ml of 1 N sodium hydroxide solution were added to a suspension of 0.63 g of the product of Step B, 30 ml of water and 10 ml of ethanol and the mixture was refluxed for one hour to obtain a clear yellow solution. The ethanol was distilled under reduced pressure and the aqueous solution was acidified with concentrated hydrochloric acid. The mixture was filtered to recover 0.6 g of imidazo-[1,2-a]-quinoxaline-2-carboxylic acid in the form of a buff crystalline solid melting at 274°–275° C.

Analysis: $C_{11}H_7N_3O_2$: Calculated: %C 61.97; %H 3.31; %N 19.71. Found: %C 61.82; %H 3.33; %N 19.71.

EXAMPLE 2 ethyl 7,8-dichloro-imidazo-[1,2-a]-quinoxaline-2-carboxylate

STEP A: 2-amino-6,7-dichloro-quinoxaline

A solution of 10 g of 4,5-dichloro-o-phenylenediamine, 9 g of alloxan hydrate, 1.5 g of boric acid and 250 ml of glacial acetic acid was stirred overnight at room temperature to obtain a brown-black solution which was filtered. The yellow-buff crystalline solid was well washed with water to obtain 15.9 g of 7,8-dichloro-alloxazine melting at >370° C. A solution of 2 g of 7,8-dichloro-alloxazine in 10 ml of concentrated sulfuric acid was slowly heated to 240° C. and held there for 10 minutes. The mixture was cooled and poured onto ice and the mixture was made alkaline with sodium hydroxide addition. The mixture was extracted several times with ether to obtain 0.73 g of 2-amino-6,7-dichloro-quinoxaline as an orange crystalline solid melting at 220° C.

Analysis: $C_8H_5N_3Cl_2$: Calculated: %C 44.89; %H 2.35; %N 19.63. Found: %C 44.96; %H 2.55; %N 19.23.

STEP B: 1-carbethoxycarbonylmethyl-2-amino-6,7-dichloro-quinoxalinium bromide A solution of 0.2 g of the product of Step A, 0.2 g of ethyl bromopyruvate and 15 ml of anhydrous tetrahydrofuran was stirred at room temperature for 24 hours and was filtered to obtain 0.1 g of 1-carbethoxycarbonylmethyl-2-amino-6,7-dichloro-quinoxalinium bromide as a pale yellow crystalline solid. The filtrate was allowed to stand for several days and was then filtered to obtain 0.065 g of the said compound as a yellowish brown solid for a total yield of 0.165 g.

STEP C: ethyl 7,8-dichloro-imidazo-[1,2-a]-quinoxaline-2-carboxylate

A suspension of 0.3 g of the product of Step B in 400 ml of ethanol was stirred at reflux for 90 minutes and the resulting solution was concentrated to about 20 ml. The mixture was filtered to obtain 0.22 g of ethyl 7,8-dichloro-imidazo-[1,2-a]-quinoxaline-2-carboxylate in the form of a soft crystalline solid melting at 297°–299° C. Crystallization of the product from ethanol yielded pale pink-white soft needles.

Analysis: $C_{13}H_9N_3O_2Cl_2$: Calculated: %C 50.32; %H 2.90; %N 13.55; %Cl 22.90. Found: %C 50.17; %H 2.93; %N 13.48; %Cl 23.30.

EXAMPLE 3

7,8-dichloro-imidazo-[1,2-a]-quinoxaline-2-carboxylic acid

A suspension of 0.5 g of the product of Example 2, 60 ml of water, 20 ml of ethanol and 20 ml of 1 N sodium hydroxide solution was stirred for 3 days during which the solid slowly dissolved to be replaced by insoluble sodium salt and the mixture was filtered. The product was suspended in 500 ml of water and the mixture was acidified to obtain 0.4 g of 7,8-dichloro-imidazo-[1,2-a] quinoxaline-2-carboxylic acid as a white crystalline solid.

I.R. Spectrum (KBr): OH at 3450 cm$^{-1}$; imidazole CH at 3140 cm$^{-1}$; and CO at 1695 cm$^{-1}$.

EXAMPLE 4

7- and 8-chloro-imidazo-[1,2-a]-quinoxaline-2-carboxylic acid

STEP A: 6- and 7-chloro-2-amino-quinoxalines

A solution of 11 g of 4-chloro-o-phenylenediamine, 10 g of alloxan hydrate, 0.64 g of boric acid and 150 ml of glacial acetic acid was stirred overnight and was filtered to obtain a pale yellow-brown crystalline solid. The latter was washed with hot water and hot ethanol to obtain 14 g of 8- and 7-chloro-alloxazines in the form of a pale yellow crystalline solid.

A solution of 10 g of the said product in 50 ml of concentrated sulfuric acid was slowly heated to 240° C. and was held there for 10 minutes. The mixture was cooled and poured onto ice and the mixture was made alkaline with sodium hydroxide. The mixture was extracted with ether and the extract was evaporated to dryness to obtain 5 g of 6- and 7-chloro-2-amino-quinozalines in the form of a yellow-crystalline solid which after crystallization from ethanol melted at 197°-203° C. Attempts to separate the isomers by chromatography and crystallization were unsuccessful.

STEP B: 1-carbethoxycarbonylmethyl-2-amino-6- and 7-chloroquinoxalinium bromides A solution of 3 g of the product of Step A, 3.5 g of ethyl bromopyruvate and 100 ml of dimethoxyethane was stirred overnight at room temperature and was filtered to obtain 3.14 g of 1-carbethoxycarbonylmethyl-2-amino-6 and 7-chloroquinoxalinium bromides as a pale yellow crystalline solid. The filtrate stood for several days and was filtered to obtain 2 more yields of 1.05 g of 0.28 g of the said product for a total yield of 4.47 g.

STEP C: ethyl 7- and 8-chloro-imidazo-[1,2-a]-quinoxaline-2-carboxylates

A suspension of 3.1 g of the product of Step B in 250 ml of ethanol was refluxed with stirring for 90 minutes and the resulting clear orange solution was concentrated and cooled. The mixture was filtered to obtain 2.0 g of a mixture of ethyl 7- and 8-chloro-imidazo-[1,2-a]-quinoxaline-2-carboxylates in the form of a pale pink-white soft crystalline solid melting at 220°-227° C. The mixture was subjected to column chromatography to obtain a pure approximately 1:1 mixture of the said isomers in the form of soft white crystalline solid melting at 231°-243° C.

Analysis: $C_{13}H_{10}N_3O_2Cl$: Calculated: %C 56.62; %H 3.63; %N 15.25. Found: %C 56.60; %H 3.74; %N 15.14.

STEP D: 7- and 8-chloro-imidazo-[1,2-a]-quinoxaline-2-carboxylic acids

A suspension of 0.6 g of the product of Step C, 60 ml of water, 20 ml of ethanol and 10 ml of 1 N sodium hydroxide solution was stirred for 2 days and was then filtered to obtain 0.54 g of a mixture of sodium salts in the form of a white, granular solid. The latter was suspended in 400 ml of water and the suspension was acidified with concentrated hydrochloric acid. The mixture was filtered to obtain 0.49 g of 7- and 8-chloro-imidazo-[1,2-a]-quinoxaline-2-carboxylic acids in the form of a white crystalline solid.

EXAMPLE 5

4-ethoxy-imidazo-[1,2-a]-quinoxaline-2-carboxylic acid

STEP A: 1-carbethoxycarbonylmethyl-2-amino-3-chloro-quinoxalinium bromide

A solution of 9 g of 2-amino-3-chloro-quinoxaline, 12 g of ethyl bromopyruvate and 180 ml of dimethoxyethane was stirred overnight and was then filtered to obtain 5.33 g of 1-carbethoxycarbonylmethyl-2-amino-3-chloro-quinoxalinium bromide as a pale yellow crystalline solid. The filtrate was stirred in the refrigerator for 2 days to obtain two additional yields of 1.20 g and 3.62 g of the product for a total yield of 10.22 g.

STEP B: ethyl 4-ethoxy-imidazo-[1,2-a]-quinoxaline-2-carboxylate

A suspension of 3.5 g of the product of Step A in 250 ml of ethanol was refluxed for one hour and the resulting clear pale yellow solution was concentrated to half its original volume and was cooled. The mixture was filtered to obtain 1.0 g of ethyl 4(5H)-oxoimidazo-[1,2-a]-quinoxaline-2-carboxylate as a white crystalline solid. The filtrate was concentrated further to obtain 1.04 g of a mixture of the said oxoimidazo compound and ethyl 4-ethoxy-imidazo-[1,2-a]-quinoxaline-2-carboxylate.
The mixture was chromatographed over silica gel and was eluted with ethyl acetate to obtain 0.55 g of ethyl 4-ethoxy-imidazo-[1,2-a]-quinoxaline-2-carboxylate as a white crystalline solid.

STEP C: 4-ethoxy-imidazo-[1,2-a]-quinoxaline-2-carboxylic acid

A suspension of 0.5 g of the product of Step B, 50 ml of water, 15 ml of ethanol and 8 ml of 1 N sodium hydroxide solution was stirred overnight to obtain a clear colorless solution which was acidified with concentrated hydrochloric acid. The mixture was filtered to obtain 4-ethoxy-imidazo-[1,2-a]-quinoxaline-2-carboxylic acid melting at 220°-222° C.

Analysis: $C_{13}H_{11}N_3O_3 - \frac{1}{2} H_2O$: Calculated: %C 58.64; %H 4.54; %N 15.78. Found: %C 59.04; %H 4.54; %N 15.74.

EXAMPLE 6

4-carbamoyl-imidazo-[1,2-a]-quinoxaline-2-carboxylic acid

STEP A: 1-carbethoxycarbonylmethyl-2-amino-3-carbamoyl-quinoxalinium bromide

A solution of 1 g of 2-amino-3-carbamoyl-quinoxaline prepared from 2-chloro-3-carbethoxy-quinoxaline by the method of Gowenlock et al [J. Chem. Soc., 1945, p. 622-5] in 50 ml of dimethoxy ethane and ethyl bromopyruvate was stirred for 2 days and was filtered to obtain 1.44 g of 1-carbethoxycarbonylmethyl-2-amino-3-carbamoyl-quinoxalinium bromide as a yellow crystalline solid.

STEP B: ethyl 4-carbamoyl-imidazo-[1,2-a]-quinoxaline-2-carboxylate

A suspension of 1 g of the product of Step A in 100 ml of ethanol was refluxed with stirring for 90 minutes and the resulting yellow solution was concentrated and cooled. The mixture was filtered to obtain 0.55 g of ethyl 4-carbamoyl-imidazo-[1,2-a]-quinoxaline-2-carboxylate as a pale yellow crystalline solid. Recrystallization from ethanol yielded soft white needles melting at 280°–284° C.

Analysis: $C_{14}H_{12}N_4O_3$: Calculated: %C 59,15; %H 4.25; %N 19.71. Found: %C 58,78; %H 4.35; %N 19.51.

STEP C:
4-carbamoyl-imidazo-[1,2-a]-quinoxaline-2-carboxylic acid

A suspension of 0.315 g of the product of Step B, 35 ml of water, 12 ml of ethanol and 6 ml of 1 N sodium hydroxide was stirred overnight to obtain a suspension of the white sodium salt which was acidified with concentrated hydrochloric acid. The mixture was filtered to obtain 0.28 g of 4-carbamoyl-imidazo-[1,2-a]-quinoxaline-2-carboxylic acid in the form of a buff crystalline solid melting at 298°–300° C.

Analysis: $C_{12}H_8N_4O_3.H_2O$: Calculated: %C 52.56; %H 3.68; %N 20.43. Found: %C 52.12; %H 3.61; %N 20.02.

EXAMPLE 7

Tri-(hydroxymethyl)-methyl-ammonium imidazo-[1,2-a]-quinoxaline-2-carboxylate

A suspension of 2.5 g of imidazo-[1,2-a]-quinoxaline-2-carboxylic acid, 1.5 g of tri-(hydroxymethyl)-methylamine and 2000 ml of methanol was refluxed with stirring until total dissolution occured and the solution was concentrated to about 70 ml and was cooled. The mixture was filtered to obtain 2.9 g (72% yield) of tri-(hydroxymethyl)-methyl-ammonium imidazo-[1,2-a]-quinoxaline-2-carboxylate melting at 242°–244° C.

Analysis: $C_{15}H_{18}N_4O_5.0.25\ H_2O$: Calculated: %C 53.17; %H 5.51; %N 16.53. Found: %C 53.13; %H 5.43; %N 16.51.

EXAMPLE 8

Sodium imidazo-[1,2-a]-quinoxaline-2-carboxylate

Aqueous 2 N sodium hydroxide solution was added dropwise to a stirred suspension of 2 g of imidazo-[1,2-a]-quinoxaline-2-carboxylic acid in 20 ml of water until dissolution occured at a pH of 9–10. Acetone was added to the mixture to cause precipitation and the mixture was filtered to obtain 1.8 g of sodium imidazo-[1,2-a]-quinoxaline-2-carboxylate melting at >300° C.

EXAMPLE 9

Tablets were prepared containing 2 mg of either imidazo-[1,2-a]-quinoxaline-2-carboxylic acid or 7,8-dichloroimidazo-[1,2-a]-quinoxaline-2-carboxylic acid or tri-(hydroxymethyl)-methyl-ammonium imidazo-[1,2-a]-quinoxaline-2-carboxylate and sufficient excipient of lactose, starch, talc and magnesium stearate for a final weight of 100 mg.

PHARMACOLOGICAL STUDY

Passive cutaneous anaphylaxis (PCA) in rats

Cutaneous anaphylaxis can be induced in rats by intradermal (ID) sensitization with antiserum followed three days later by systemic challenge with antigen. Evans blue dye injected with the antigen is used as a marker to assess the severity of the local response. Antiallergic drugs inhibit this reaction. This method has been described by OVARY (1962) "Passive Cutaneous Anaphylaxis in Allergology" Page 358–367 Ed. Brown: Pergamon Press:-male rats weighing 180–220 grams are used in groups of seven.

Preparation of Antigen for Sensitization (Alum precipitated ovalbumen)

1. Wash 120 grams of $Al(OH)_3$ gel in 140 ml of saline (use of a macerater facilitates mixing).
2. Centrifuge at 3,000 r.p.m. for about 10 minutes.
3. Resuspend the precipitate with 300 ml of albumen egg powder (1.3 mg/ml) in saline and allow to stand for 30 minutes.
4. Centrifuge at 3,000 r.p.m. for 10 minutes.
5. Weigh the wet precipitate and to each gram weight add 1 ml of saline. Store in refrigerator (Quantity sufficient for 60 rats for a 3 day sensitization program).

Preparation of Antiserum (anti-ovalbumen)

1 ml of the alum precipitated ovalbumen was injected subcutaneously into rats weighing 180–200 grams on days 0,2,4. The rats were bled on day 14 either by cardiac puncture of via the dorsal abdominal aorta. Equal quantities of serum from each animal were pooled and thoroughly mixed and 2 ml aliquots were stored at $-20°$ C. in plastic tubes.

Serum Dilution for PCA

The antiserum for sensitization was diluted so that an ID injection of 0.1 ml into control animals would give an average score of a single spot of between 2.0–3.5 using a 4 point scoring system.

Method (A) SENSITIZATION: The rats were anaesthetized with Nembutal (40–60 mg/kg i.p.) and were then sensitized by four ID injections (0.1 ml each) on their shaved backs. The animals were then left for a period of three days to develop sensitization.

(B) CHALLENGE: The sensitized rats were dosed orally or intraveneously with the drug immediately prior to intraveneous challenge via the superficial penile vein with 1 ml of an antigen/Evans blue mixture (1 mg albumen egg powder in 0.5 ml saline plus 0.5 ml of 1% Evans blue). The injections were speeded up by using an automatic 1 ml self-filling glass syringe. The "challenged" rats were killed after 30 minutes, (usually pithed) and their skin on the dorsal surface was removed. The degree and area of blueing, proportional to the anaphylactic reaction was assessed on a four point scoring system.

Calculations

1. Total scores for sites 1,2,3 and $4 = X$
2. Mean value of X for each group $= \overline{X}$
3. $\overline{X}\ t = \overline{X}$ for test group; $\overline{X}\ c = \overline{X}$ for control group 4. $\%\ \text{inhibition} = \dfrac{\overline{X}c - \overline{X}t}{\overline{X}c} \times \dfrac{100}{1}$ 5. $ED_{50} =$ dose of drug giving 50% inhibition.

$ED_{50}$ values for the compounds tested in the passive cutaneous anaphylaxis screen (in rats) are as follows:

| COMPOUND OF EXAMPLE | ED 50 in mg/kg | |
|---|---|---|
| | Intraveinously | Orally |
| 1 | 0.073 | 0.73 |
| 3 | 0.20 | — |

-continued

| COMPOUND OF EXAMPLE | ED$_{50}$ in mg/kg | |
|---|---|---|
| | Intraveinously | Orally |
| 4 | 0.12 | 0.71 |
| 5 | 0.83 | — |
| 6 | 3.13 | — |
| 7 | 0.073 | — |

Various modifications of the products and methods of the invention may be made without departing from the spirit or scope thereof and it is to be understood that the invention is intended to be limited only as defined in the appended claims.

We claim:

1. A compound selected from the group consisting of imidazoquinoxalines of the formula wherein R is selected from the group consisting of hydrogen, alkyl of 1 to 5 carbon atoms, —NH$_4$, alkali metal, alkaline earth metal, magnesium, aluminum and non-toxic, pharmaceutically acceptable amines, X is selected from the group consisting of hydrogen, alkoxy of 1 to 5 carbon atoms and carbamoyl and Y and Z are individually selected from the group consisting of hydrogen and halogen and their non-toxic, pharmaceutically acceptable acid addition salts.

2. A compound of claim 1 wherein R is selected from the group consisting of hydrogen and ethyl, X is selected from the group consisting of hydrogen and ethoxy and Y and Z are individually selected from the group consisting of hydrogen and chlorine.

3. A compound of claim 2 wherein R is hydrogen.

4. A compound of claim 1 wherein R, X and Z are hydrogen and Y is selected from the group consisting of hydrogen and chlorine.

5. A compound of claim 1 selected from the group consisting of imidazo-[1,2-a]-quinoxaline-2-carboxylic acid and its non-toxic, pharmaceutically acceptable acid addition salts.

6. A compound of claim 1 selected from the group consisting of ethyl 7,8-dichloro-imidazo-[1,2-a]-quinoxaline-2-carboxylate and its non-toxic, pharmaceutically acceptable acid addition salts.

7. A compound of claim 1 selected from the group consisting of 7,8-dichloro-imidazo-[1,2-a]-quinoxaline-2-carboxylic acid, and its non-toxic, pharmaceutically acceptable acid addition salts.

8. A compound of claim 1 selected from the group consisting of 7-chloro-imidazo-[1,2-a]-quinoxaline-2-carboxylic acid and its non-toxic, pharmaceutically acceptable acid addition salts.

9. A compound of claim 1 selected from the group consisting of 8-chloro-imidazo-[1,2-a]-quinoxaline-2-carboxylic acid and its non-toxic, pharmaceutically acceptable acid addition salts.

10. A compound of claim 1 selected from the group consisting of 4-ethoxy-imidazo-[1,2-a]-quinoxaline-2-carboxylic acid, and its non-toxic, pharmaceutically acceptable acid addition salts.

11. A compound of claim 1 selected from the group consisting of 4-carbamoyl-imidazo-[1,2-a]-quinoxaline-2-carboxylic acid and its non-toxic, pharmaceutically acceptable acid addition salts.

12. A compound of claim 1 which is tri-(hydroxymethyl)methyl-ammonium imidazo-[1,2-a]-quinoxaline-2-carboxylate.

13. A compound of claim 1 which is sodium imidazo-[1,2-a]-quinoxaline-2-carboxylate.

14. An antiallergic composition comprising an antiallergically effective amount of at least one compound of claim 1 and an excipient.

15. A composition of claim 14 wherein R is selected from the group consisting of hydrogen and ethyl, X is selected from the group consisting of hydrogen and ethoxy and Y and Z are individually selected from the group consisting of hydrogen and chlorine.

16. A composition of claim 15 wherein R is hydrogen.

17. A composition of claim 14 wherein R, X and Z are hydrogen and Y is hydrogen or chlorine.

18. A composition of claim 14 wherein the compound is selected from the group consisting of imidazo-[1,2-a]-quinoxaline-2-carboxylic acid and its non-toxic, pharmaceutically acceptable acid addition salts.

19. A composition of claim 14 wherein the compound is selected from the group consisting of ethyl 7,8-dichloroimidazo-[1,2-a]-quinoxaline-2-carboxylate, and its non-toxic, pharmaceutically acceptable acid addition salts.

20. A composition of claim 14 wherein the compound is selected from the group consisting of 7,8-dichloro-imidazo-[1,2-a]-quinoxaline-2-carboxylic acid, and its non-toxic, pharmaceutically acceptable acid addition salts.

21. A composition of claim 14 wherein the compound is selected from the group consisting of 7-chloro-imidazo-1,2-a]-quinoxaline-2-carboxylic acid, and its non-toxic, pharmaceutically acceptable acid addition salts.

22. A composition of claim 14 wherein the compound is selected from the group consisting of 8-chloro-imidazo-1,2-a]-quinoxaline-2-carboxylic acid, and its non-toxic, pharmaceutically acceptable acid addition salts.

23. A composition of claim 14 wherein the compound is selected from the group consisting of 4-ethoxy-imidazo-1,2-a]-quinoxaline-2-carboxylic acid, and its non-toxic, pharmaceutically acceptable acid addition salts.

24. A composition of claim 14 wherein the compound is selected from the group consisting of 4-carbamoyl-imidazo-[1,2-a]-quinoxaline-2-carboxylic acid, and its non-toxic, pharmaceutically acceptable acid addition salts.

25. A composition of claim 14 wherein the compound is tri-(hydroxymethyl)-methyl-ammonium imidazo-[1,2-a]-quinoxaline-2-carboxylate.

26. A composition of claim 14 wherein the compound is sodium imidazo-[1,2-a]-quinoxaline-2-carboxylate.

27. A method of relieving allergic symptoms in warm-blooded animals comprising administering to warm-blooded animals an antiallergically effective amount of at least one compound of claim 1.

28. The method of claim 27 wherein R is selected from the group consisting of hydrogen and ethyl, X is selected from the group consisting of hydrogen and ethoxy and Y and Z are individually selected from the group consisting of hydrogen and chlorine.

29. The method of claim 28 wherein R is hydrogen.

30. The method of claim 27 wherein R, X and Z are hydrogen and Y is hydrogen or chlorine.

31. The method of claim 27 wherein the compound is imidazo-[1,2-a]-quinoxaline-2-carboxylic acid.

32. The method of claim 27 wherein the compound is ethyl 7,8-dichloro-imidazo-[1,2-a]-quinoxaline-2-carboxylate.

33. The method of claim 27 wherein the compound is 7,8-dichloro-imidazo-[1,2-a]-quinoxaline-2-carboxylic acid.

34. The method of claim 27 wherein the compound is 7-chloro-imidazo-[1,2-a]-quinoxaline-2-carboxylic acid.

35. The method of claim 27 wherein the compound is 8-chloro-imidazo-[1,2-a]-quinoxaline-2-carboxylic acid.

36. The method of claim 27 wherein the compound is 4-ethoxy-imidazo-[1,2-a]-quinoxaline-2-carboxylic acid.

37. The method of claim 27 wherein the compound is 4-carbamoyl-imidazo-[1,2-a]-quinoxaline-2-carboxylic acid.

38. The method of claim 27 wherein the compound is tri-(hydroxymethyl)-methyl-ammonium imidazo-[1,2-a]-quinoxaline-2-carboxylate.

39. The method of claim 27 wherein the compound is sodium imidazo-[1,2-a]-quinoxaline-2-carboxylate.

* * * * *